(12) United States Patent
Avellanet

(10) Patent No.: US 6,264,664 B1
(45) Date of Patent: Jul. 24, 2001

(54) SURGICAL BASKET DEVICES

(75) Inventor: Francisco J. Avellanet, Coral Gables, FL (US)

(73) Assignee: General Science and Technology Corp., Miami, FL (US)

( * ) Notice: Subject to any disclaimer, the term of this patent is extended or adjusted under 35 U.S.C. 154(b) by 0 days.

(21) Appl. No.: 09/523,233

(22) Filed: Mar. 10, 2000

(51) Int. Cl.$^7$ ...................................................... A61B 17/00
(52) U.S. Cl. ................................ 606/128; 606/127; 606/1
(58) Field of Search ..................................... 606/128, 127, 606/170, 171, 185, 1, 113, 114, 115

(56) References Cited

U.S. PATENT DOCUMENTS

| | | | |
|---|---|---|---|
| 5,057,114 | * 10/1991 | Wittich et al. | 606/127 |
| 5,064,428 | * 11/1991 | Cope et al. | 606/127 |
| 5,176,688 | * 1/1993 | Narayan et al. | 606/128 |
| 5,342,371 | * 8/1994 | Welter et al. | 606/113 |
| 5,860,972 | * 1/1999 | Hoang | 606/128 |
| 6,015,415 | * 1/2000 | Avellanet | 606/113 |
| 6,174,318 | * 1/2001 | Bates et al. | 606/127 |

* cited by examiner

*Primary Examiner*—Pedro Philogene
(74) *Attorney, Agent, or Firm*—David P. Gordon; David S. Jacobson; Thomas A Gallagher

(57) ABSTRACT

Surgical basket instruments according to the invention generally include a sheath (catheter), a shaft extending through and axially movable relative to the sheath, a basket assembly coupled to a distal end of the shaft, and a handle coupled to a proximal end of the shaft and adapted for facilitating movement of the shaft relative to the sheath such that the basket assembly may be moved out of and into the distal end of the sheath. The basket assembly is formed from a plurality of circumferentially spaced flexible wires or cables which facilitate entrapping of urological and gastrointestinal calculi. The shaft is made of a hollow compacted cable formed from a flexible yet strong shape memory material such as a nickel-titanium alloy. The hollow (channel) in the shaft receives at least one fiber optic couplable to a laser beam for destroying calculi. The fiber optic may be stationary or axially movable relative to the shaft, and may extend to the proximal end of the basket assembly or beyond the distal tip of the instrument so as to act as a sphinctertome. In one embodiment, additional fiber optics which extend through the channel, and a fluid source coupled to the channel permit the basket instrument to have the additional functionality of an endoscope.

27 Claims, 13 Drawing Sheets

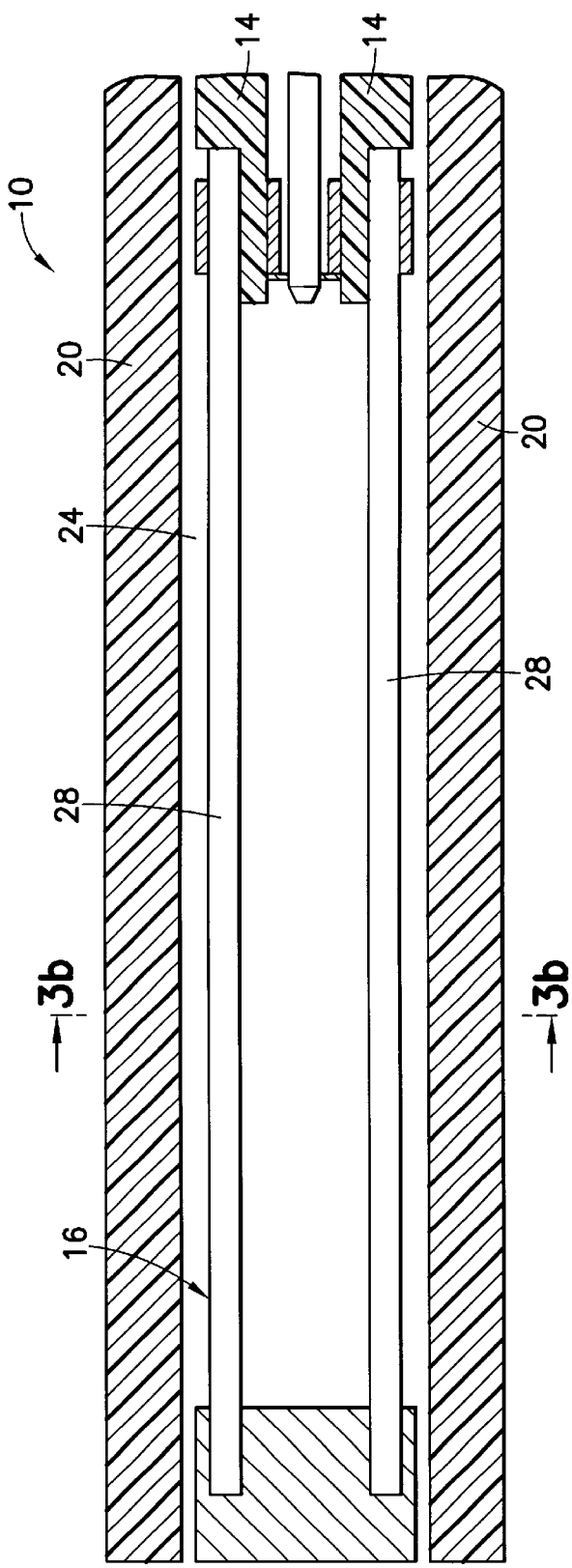
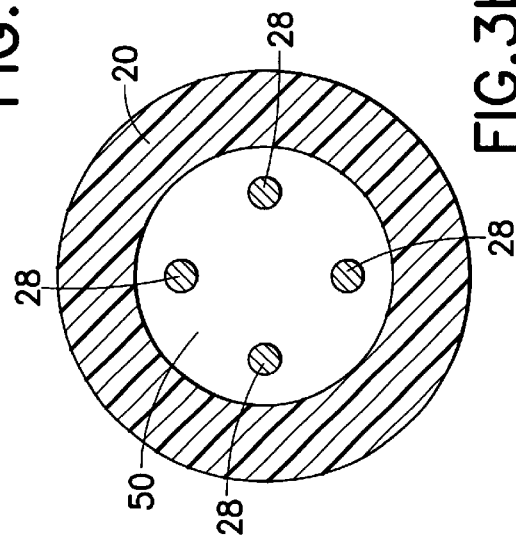
FIG.3a
FIG.3b

SURGICAL BASKET DEVICES

BACKGROUND OF THE INVENTION

1. Field of the Invention

This invention relates broadly to medical instruments. More particularly, this invention relates to basket devices for retrieving calculi located in the urological and gastrointestinal ducts. This invention can also be used to retrieve foreign objects from various locations within the mammalian body.

2. State of the Art

Surgical basket instruments are inserted into endoscopes and are typically used to remove calculi in the form of kidney stones, gallstones, biliary stones, and the like from the body without requiring a large incision. The basket instruments generally include a shaft having a resilient basket assembly coupled (for example, via crimping, welding, or soldering) to the distal end thereof, and a sheath (catheter) through which the shaft is axially extendable. The basket assembly is generally formed from resilient strands defining a cage-like enclosure. The basket assembly is radially collapsible to fit within the sheath, but distal movement of the shaft relative to the sheath enables the basket assembly to be moved beyond the distal end of the sheath. A wire, cable, or other mechanism, coupled proximally to the shaft at a handle and distally to the basket, is used to manipulate and expand and contract the extended basket. When the basket is in an expanded state, the basket may be maneuvered to envelop a calculus. The shaft may then be moved relative to the sheath to collapse the basket around the calculus and secure the calculus therein. The entire instrument is then withdrawn from the body of the patient along with the calculus. In addition, baskets may be expanded within a vein and rotated to function as a filter or thrombectomy device.

Several different basket designs are known in the art. For example, U.S. Pat. No. 5,064,428 to Cope et al., U.S. Pat. No. 4,611,594 to Grayhack et al., and U.S. Pat. Nos. 5,496,330 and 5,788,710 both to Bates et al. disclose prior art basket assemblies, and are hereby incorporated by reference herein in their entireties. U.S. Pat. No. 5,176,688 to Narayan et al., discloses an endoscopic basket instrument for use with a multi-bore endoscope having a first bore provided for operating a basket assembly, a second bore provided for a hammer, and a third bore for an optical system, and is hereby incorporated by reference herein in its entirety. U.S. Pat. No. 5,057,114 to Wittich et al. discloses an endoscopic basket instrument having a basket formed from superelastic metallic alloy wires, and is hereby incorporated by reference herein in its entirety.

However, the medical community has not been satisfied with the currently available basket instruments. In particular, with the instruments of the prior art, it is relatively difficult to visualize the surroundings at the distal end of the basket assembly especially when the basket contains a large calculus, adequately steer the instrument through the tortuous urological or gastrointestinal tracts, and adequately surround and capture a large calculus. One reason is the inability of the physician to fluoroscopically visually monitor the distal end of the basket assembly during the procedure such that the physician can best steer the basket assembly and attempt calculus entrapping. Further, the instruments of the prior art require that relatively complex mechanisms be built within the basket device to crush the calculi into smaller particles once captured or to obliterate the calculi altogether.

SUMMARY OF THE INVENTION

It is therefore an object of the invention to provide a basket instrument having a basket assembly which facilitates positioning the instrument to more adequately entrap calculi in the basket assembly for removal from the urological and gastrointestinal systems.

It is a further object of the invention to provide a basket instrument providing a pathway which can accommodate a laser which destroys objects within the basket.

It is another object of the invention to provide a basket instrument providing a channel for an optical device to allow the physician to better visualize, steer, and monitor the movement of the basket and locate the calculi to facilitate entrapment.

A further object of the invention is to provide a basket instrument having a laser extending beyond a distal end of the instrument which can be used as a sphinctertome.

Another object of the invention to provide a basket instrument which provides the ability to both view the surroundings at a distal end of the instrument and operate a laser which destroys objects within the basket.

In accord with these objects, which will be discussed in detail below, the surgical basket instrument of the invention generally includes a sheath (catheter), a hollow shaft extending through and axially movable relative to the sheath, a basket assembly coupled to a distal end of the shaft, and an activation handle coupled to a proximal end of the shaft and adapted for facilitating movement of the shaft relative to the sheath such that the basket assembly may be moved out of and into the distal end of the sheath. The basket assembly is formed from a plurality (e.g. three or more) of circumferentially spaced flexible wires or cables which facilitate entrapping of urological and gastrointestinal calculi. It is preferred that the hollow shaft be constructed from a compacted cable formed from a plurality of wires or cables which have been first twisted about a core and then drawn through at least one die (i.e. compacted) as is disclosed in greater detail (Docket # AVE-039) and U.S. Ser. No. 09/476,195 both to Avellanet, which are hereby incorporated by reference herein in their entireties. More particularly, a channel is formed within the shaft by removing the core after the wires or cables forming the exterior of the shaft have been compacted. Preferably, the channel extends axially through the center of the entire shaft, and the shaft extends from the proximal end of the instrument to the proximal end of the basket assembly. However, the shaft may be adapted to extend to or beyond the distal end of the basket assembly. It is preferable that the shaft be formed from a flexible yet strong material such as a nickel-titanium alloy.

According to a first embodiment of the invention, a fiber optic is attached within the channel in the shaft and extends to the proximal end of the basket assembly. The fiber optic is adapted to carry a laser beam for destroying calculi contained within the basket assembly. The channel of the shaft is substantially enclosed at the distal end of the shaft. The channel is substantially enclosed at the distal end of the shaft by a shield which substantially surrounds but does not block a tip of the fiber optic.

According to a second embodiment, the fiber optic is axially movable within the shaft, and may extend into the basket assembly and beyond the distal end of the instrument.

According to a third embodiment of the invention, at least a pair of fiber optics extend within the channel in the shaft to the distal end of the shaft. One of the pair of the fiber optics is used to send light down the shaft. The other of the pair may be used to visualize the calculi and the surroundings. Either of the pair may also be adapted to receive a laser for destroying calculi contained within the basket. Alternatively, a third fiber optic is adapted to receive the laser. Additionally, a proximal source of fluid useful in cleaning the visualization optic is coupled to and in fluid communication with the channel of the shaft.

According to a fourth embodiment, a shaft having a channel is extended through the basket assembly and beyond the distal end of the instrument. A fiber optic, adapted to receive a laser, is attached within the channel and extends beyond to the distal end of the shaft. The laser operates as a sphinctertome, to cut a pathway into a bile duct or other sphincter enabling insertion of the basket assembly into the duct.

Additional objects and advantages of the invention will become apparent to those skilled in the art upon reference to the detailed description taken in conjunction with the provided figures.

BRIEF DESCRIPTION OF THE DRAWINGS

FIG. 3a is a broken cross-sectional view of the distal end of the first embodiment with the basket assembly retracted within the sheath;

FIG. 3b is a cross-sectional view taken along line 3b—3b of FIG. 3a according to the invention;

DETAILED DESCRIPTION OF THE PREFERRED EMBODIMENTS

Figure 1:
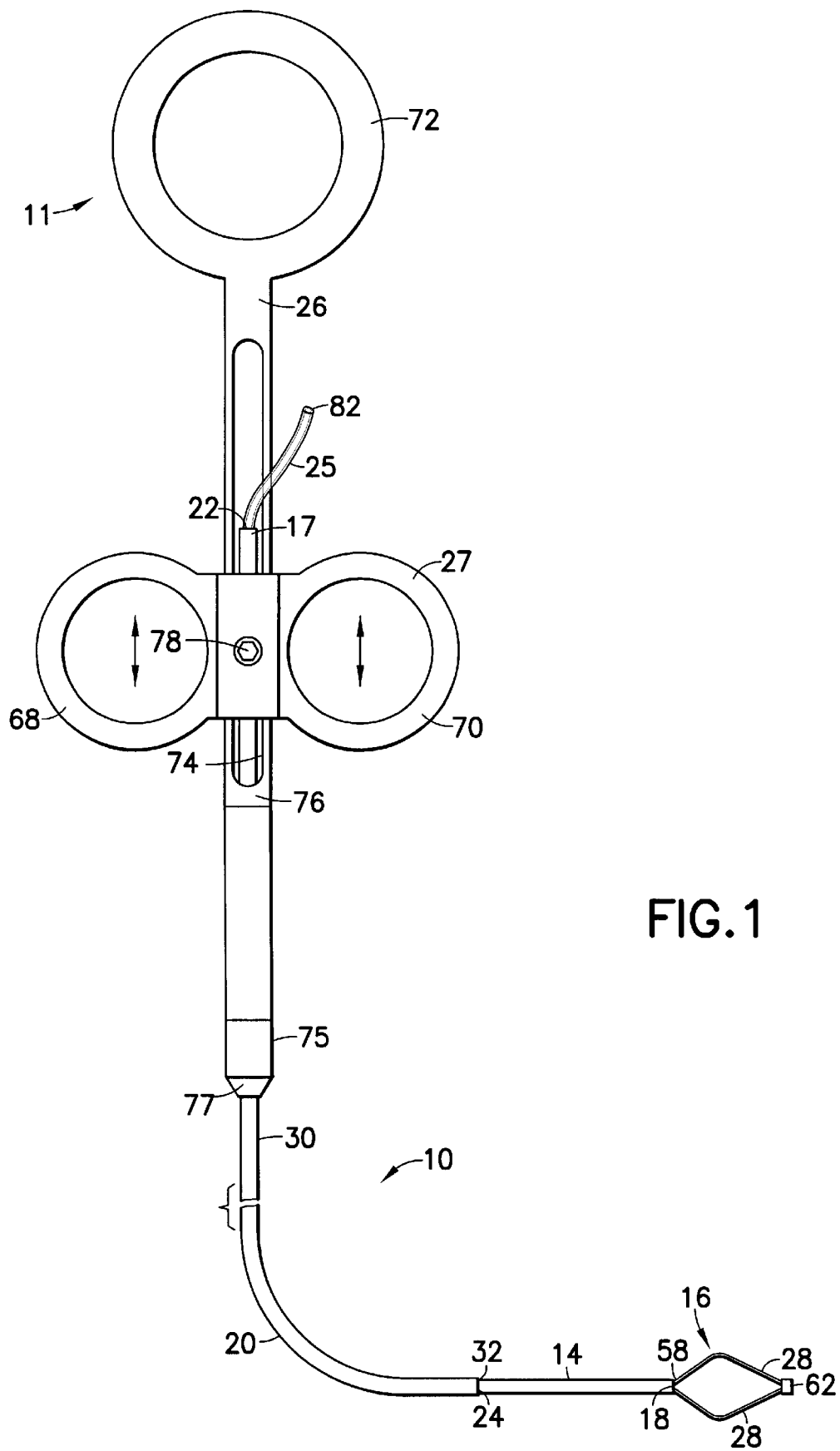
FIG. 1 is a partial broken side elevation of an exemplary first embodiment of the surgical basket instrument according to the invention.
Figure 2:
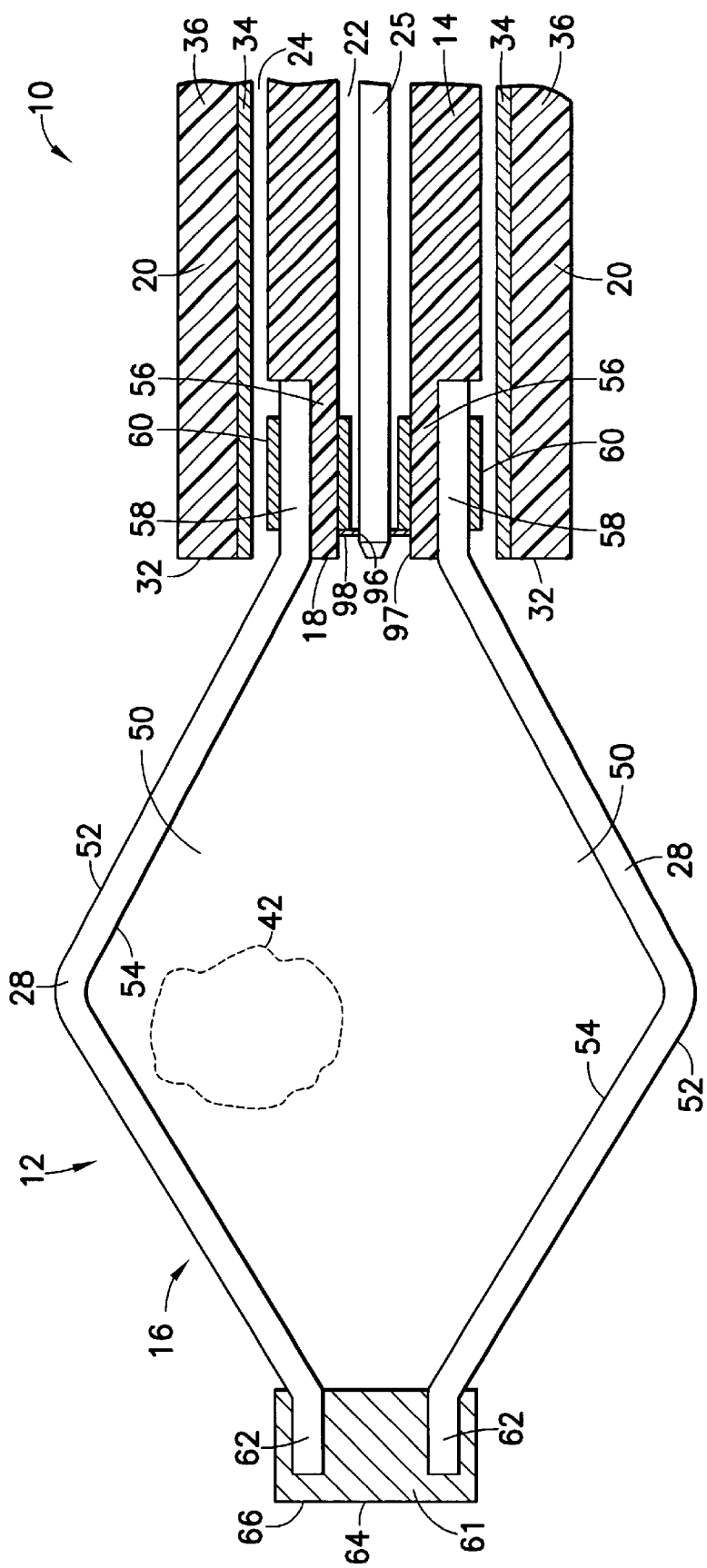
FIG. 2 is a broken cross-sectional view of the distal end of a first embodiment of the surgical basket instrument according to the invention, with a basket assembly extended.

Turning now to FIGS. 1 and 2, a first embodiment of a surgical basket instrument 10 is shown. The instrument 10 has a proximal handle assembly 11, a flexible hollow shaft 14 having a proximal end 17 and a distal end 18 and defining a channel 22 therethrough, a basket assembly 16 having a proximal end 58 coupled to the distal end 18 of the shaft 14 and a distal end 62, and a preferably Teflon®, or Teflon®-coated HDPE, hollow sheath (catheter) 20 having a proximal end 30 and a distal end 32 and defining an axial pathway 24 therethrough into which the shaft 14 and basket assembly 16 are inserted. Additionally, a fiber optic 25 having a proximal end 82 attachment site extends through the length of the channel 22 to the distal end 18 of the shaft 14. According to the first embodiment, the fiber optic 25 is preferably coupled to the shaft 14 to prevent the distal end of the fiber optic 25 from moving relative to the shaft. A viewing device and/or a laser is couplable to a proximal end 82 of the fiber optic 25.

The handle assembly 11 includes a stationary handle piece 26 coupled to the sheath 20, and a movable handle piece 27 coupled to the shaft 14. The exemplary proximal handle 11 is shown which is similar to that disclosed in detail in U.S. Pat. No. 5,3423,371 to Welter et al., which is hereby incorporated by reference herein in its entirety. An alternate exemplary handle (not shown) is disclosed in U.S. Ser. No. 09/237,420 to Avellanet, which is hereby incorporated by reference herein in its entirety. Specifically, the exemplary handle 11 includes the stationary handle piece 26 and the movable handle piece 27. A distal end 75 of a tubular portion 76 of the stationary handle piece 26 is connected to the proximal end 30 of the sheath 20. Preferably, the tubular portion 76 includes a hollow rotatable coupling 77 (e.g. hollow bearing or hollow bushing) coupled between the distal end 75 of the tubular portion 76 and the proximal end 30 of the sheath 20 through which the shaft 14 runs, allowing rotation of the sheath 20 relative to the stationary handle piece 26 (and the shaft 14). The movable handle piece 27 is connected to the proximal end 17 of the shaft 14. To operate the basket instrument 10, the physician places his/her index and middle fingers in rings 68, 70 in the movable handle piece 27 and his/her thumb into a ring 72 at the end of the stationary handle piece 26 and slides the two handle pieces relative to each other. A slider (not shown) is positioned through a longitudinal slot 74 of the tubular portion 76 of the stationary handle piece 26 and is coupled to the shaft 14. The slider is longitudinally moveable within the slot 74 to move the shaft 14 axially relative to the sheath 20, and is secured therein, preferably by a set screw 78. In this manner, the shaft 14, fiber optic 25, and basket assembly 16 may be retracted into the sheath 20 or extended beyond the distal end 32 of the sheath 20. Once extended, the basket assembly 16 may be moved and manipulated (e.g. rotated) to capture calculi 42, and then returned to within the sheath 20 to retain the calculi 42 for withdrawal through a scope and from the human body. By way of example, when the basket 16 is not extended (i.e. the sheath 20 surrounds the shaft 14 and basket assembly 16, as seen in FIG. 3a), the movable hand piece 27 is closest the ring 72 of the stationary handle piece 26. As shown in FIG. 1, when the shaft 14 and basket 16 are fully extended, the movable handle piece 27 is furthest from the ring 72 of the stationary handle piece 26.

The sheath 20 is preferably made of a highly lubricous co-extrusion of an inner material 34 and an outer material 36. Preferably the inner material 34 has sufficient lubricity to reduce the friction between the shaft 14 and the sheath 20 during extension and rotation of the basket 16. The outer material 36 may also be hydrophilically coated for increased lubricity while the basket instrument 10 is being inserted slidably into a scope and through the anatomical passageways. Exemplar co-extrusions include an inner material 34 of HDPE or PTFE and an outer material 36 of nylon.

The hollow shaft 14, which is movable in and out of the sheath 20, is preferably formed from a cable having a central channel 22 of diameter "d" defined axially along the entire length of the shaft 14. The channel 22 receives a fiber optic 25 therein which extends to the distal end 18 of the shaft 14 to the basket assembly 16. The fiber optic 25 is adapted to carry a laser beam for destroying calculi 42 captured within the basket assembly 16. The fiber optic 25 is preferably clad to prevent light from escaping along the length of the fiber optic 25. A shield 98, which substantially blocks a distal end 97 of the channel 22, is provided across the channel 22 adjacent the distal end 18 of the shaft 14. The shield 98 defines a hole 96 through which the fiber optic 25 extends. The fiber optic 25 is used for directing laser light at larger calculi 42. These large calculi 42 would normally require mechanical lithotripsy or ultrasonic lithotripsy for disintegration. However, the laser energy facilitates a break-up of the calculi 42 into pieces which may be retrieved in the basket 16.

Figure 4:
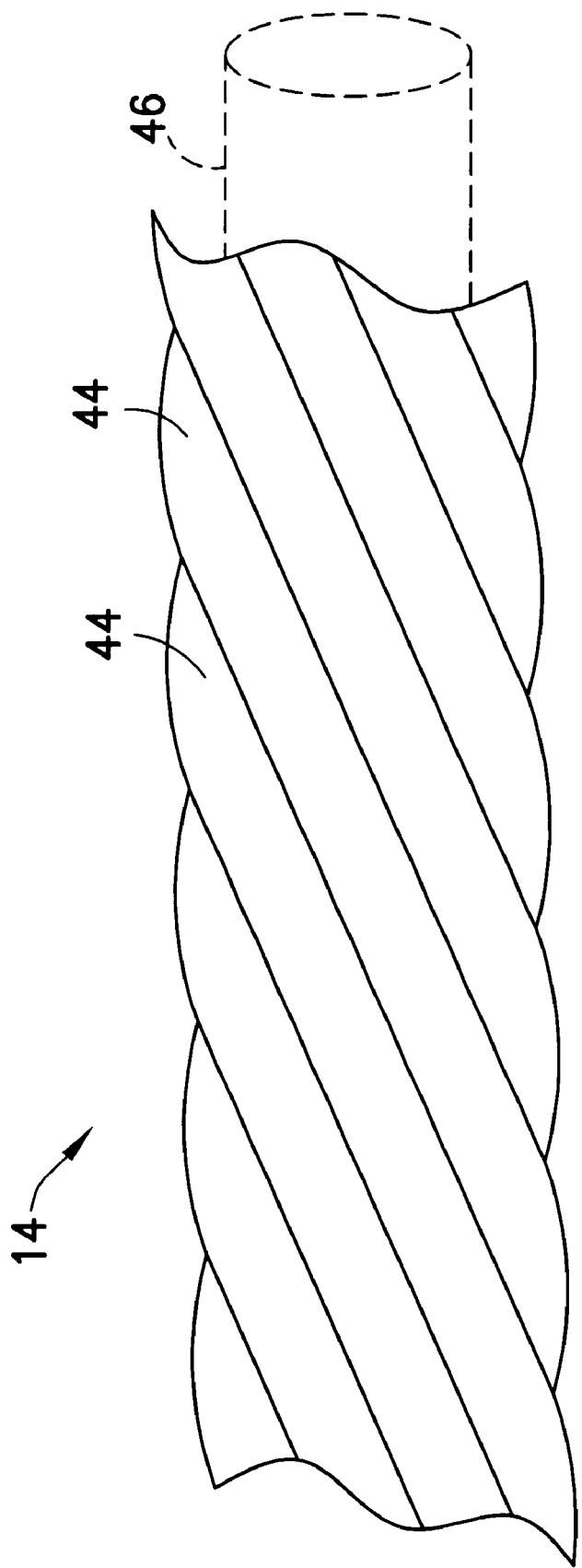
FIG. 4 is a broken perspective view of a multi-filament cable twisted about a central core used in making the shaft of FIG. 2.

More particularly, as shown in FIG. 4, the hollow shaft 14 is preferably constructed from a plurality (typically three or more) of stainless steel or nickel-titanium wires 44 which have been twisted about a central core 46 having a desired diameter and then drawn through a series of dies (i.e., compacted) to produce a cable having a substantially smooth exterior diameter of a desired size. The preferably centrally aligned channel (seen better in FIG. 2) is defined in the shaft 14 by removing the central core 46 from within the compacted cable after the cable is compacted. The manufacture of twisted and drawn cables is disclosed in co-owned and co-pending U.S. Ser. Nos. 08/856,571 to Avellanet et al., 08/843,405 and 08/963,686 to Avellanet, 09/044,203 and 09/087,476 to Avellanet et al., 09/048,746 to Bales et al., and 09/060,969 to Avellanet, which are hereby incorporated by reference herein in their entireties. In this embodiment, the outer diameter of the shaft 14 is preferably between 0.062 (¹⁄₁₆) inches and 0.250 (¼) inches, depending on the application, and the inner diameter is between 0.031 (¹⁄₃₂) inches and 0.20 (⅕) inches. Cables made from twisted and drawn wires (i.e., compacted cables) are more torqueable and flexible than a single wire or other cables of the same exterior diameter as the twisted and drawn cable, and therefore permit a greater degree of steerability than capable with prior art basket instruments. For example (referring to FIG. 1), a physician may provide a torquing motion to a proximal end 17 of the shaft 14 (by rotating the handle 11 which is coupled to the shaft 14) which will result in angular movement of a distal end 12 of the instrument 10 (i.e., the basket 16). In particular with the preferred cable, rotating the handle 11 360° will result in the distal end 18 of the shaft 14 and the basket 16 rotating a full 360°.

Referring again to FIGS. 1 and 2, the basket assembly 16 preferably includes three or more axially extending members 28 coupled circumferentially about the distal end 18 of the shaft 14. The members 28 are preferably cables made from a highly elastic material having shape memory and/or superelastic properties (including twisted and drawn Nitinol which is taught in the above-referenced and previously incorporated co-pending applications). Alternately, the members 28 forming the basket assembly 16 may be made from solid wire or standard cable such as stainless steel wires, highly radiopaque metal wires, e.g., gold or platinum wires, or a combination of any of the preceding, or any highly flexible shape memory wires which are also taught in the above-referenced and previously incorporated co-pending applications, so long as the basket assembly 16 has adequate suppleness and has shape memory properties. The members 28 are trained or otherwise formed to radially curve away from the axis of the shaft 14 when the basket 16 is moved beyond the sheath 20. As shown in FIG. 3a and in cross-section in FIG. 3b, when the shaft 14 and basket assembly 16 are within the hollow 24 of the sheath 20, the members 28 of the basket assembly 16 are deformed from their pre-formed shape.

Referring again t6 FIG. 2, as previously mentioned, when the shaft 14 is moved forward in the sheath 20 thereby exposing the basket assembly 16, the pre-formed members automatically expand to take their pre-formed shape. Together the members 28 form the cage-like basket 16 defining spaces 50 between the members 28 through which calculi 42 may be maneuvered into the basket 16. The members 28 may be designed to expand radially, spherically, or otherwise non-symmetrically to provide larger spaces 50 between some of the members 28 to better capture larger calculi 42. The outer portions 52 of the members 28 are preferably coated in a Teflon® or hydrophilic coating to reduce friction between the basket 16 and walls of the duct (not shown) in which the basket 16 is maneuvered, while the inner portions 54 preferably remain uncoated to facilitate grabbing the calculi 42. Preferably, the distal end 18 of the shaft 14 is formed having an attachment portion 56 to which a proximal end 58 of the basket assembly 16 attaches. However the attachment portion 56 may alternatively be formed at other locations along the length of the shaft 14. The members 28 forming the basket assembly 16 are preferably coupled to the attachment portion 56 adjacent the distal end 18 of the shaft 14 by crimping, welding, adhering with adhesive, or soldering a crimp band or a proximal ferrule 60 about both the attachment portion 56 of the shaft 14 and the proximal end 58 of the members 28 of the basket assembly 16 such that the fiber optic 25 is not blocked. Similarly, the members 28 at the distal end 62 of the basket assembly 16 are coupled by a crimp band, cap, or distal ferrule 61 forming a tip 66 of the instrument 10 when the basket 16 is extended.

Figure 5:
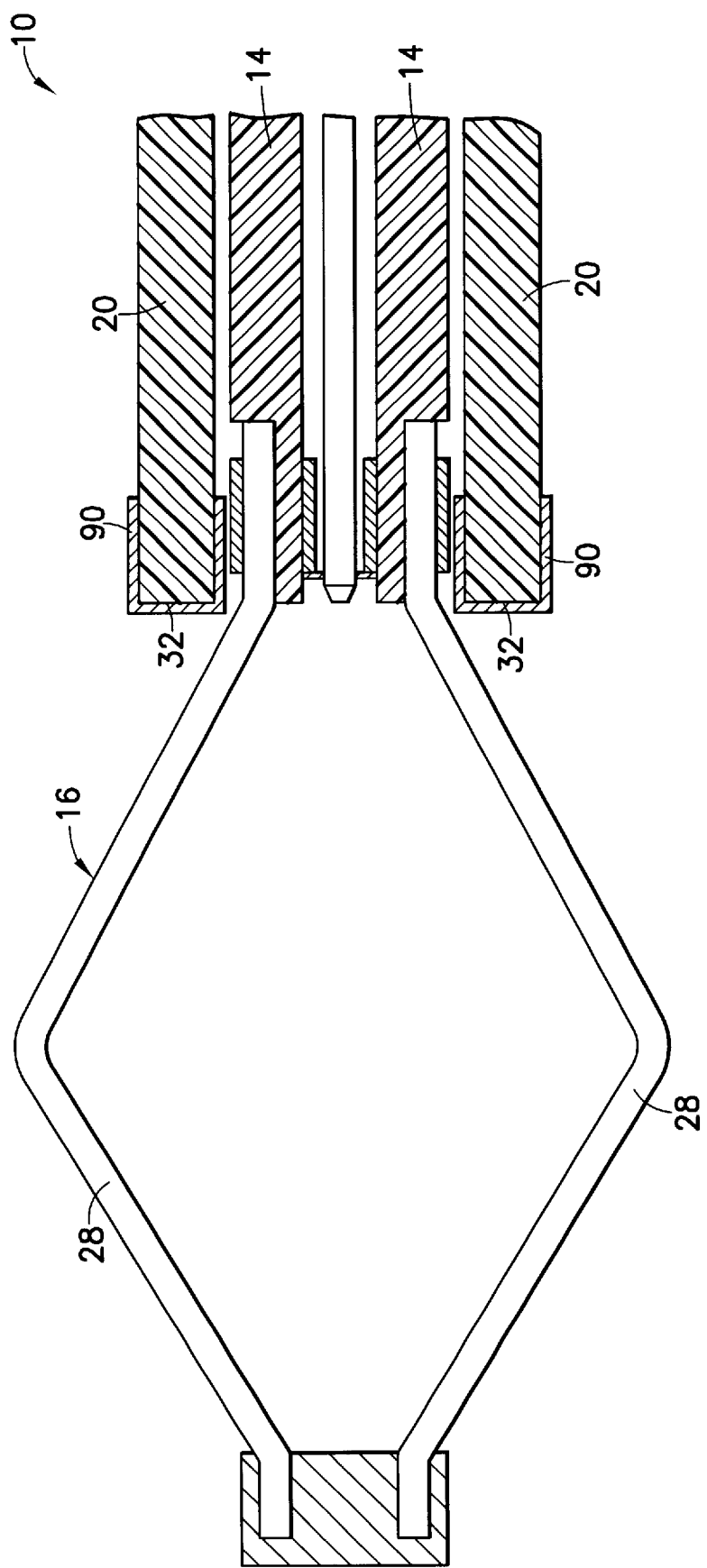
FIG. 5 is a broken cross-sectional view of the first embodiment of the invention showing a first preferred aspect of the invention.
Figure 6:
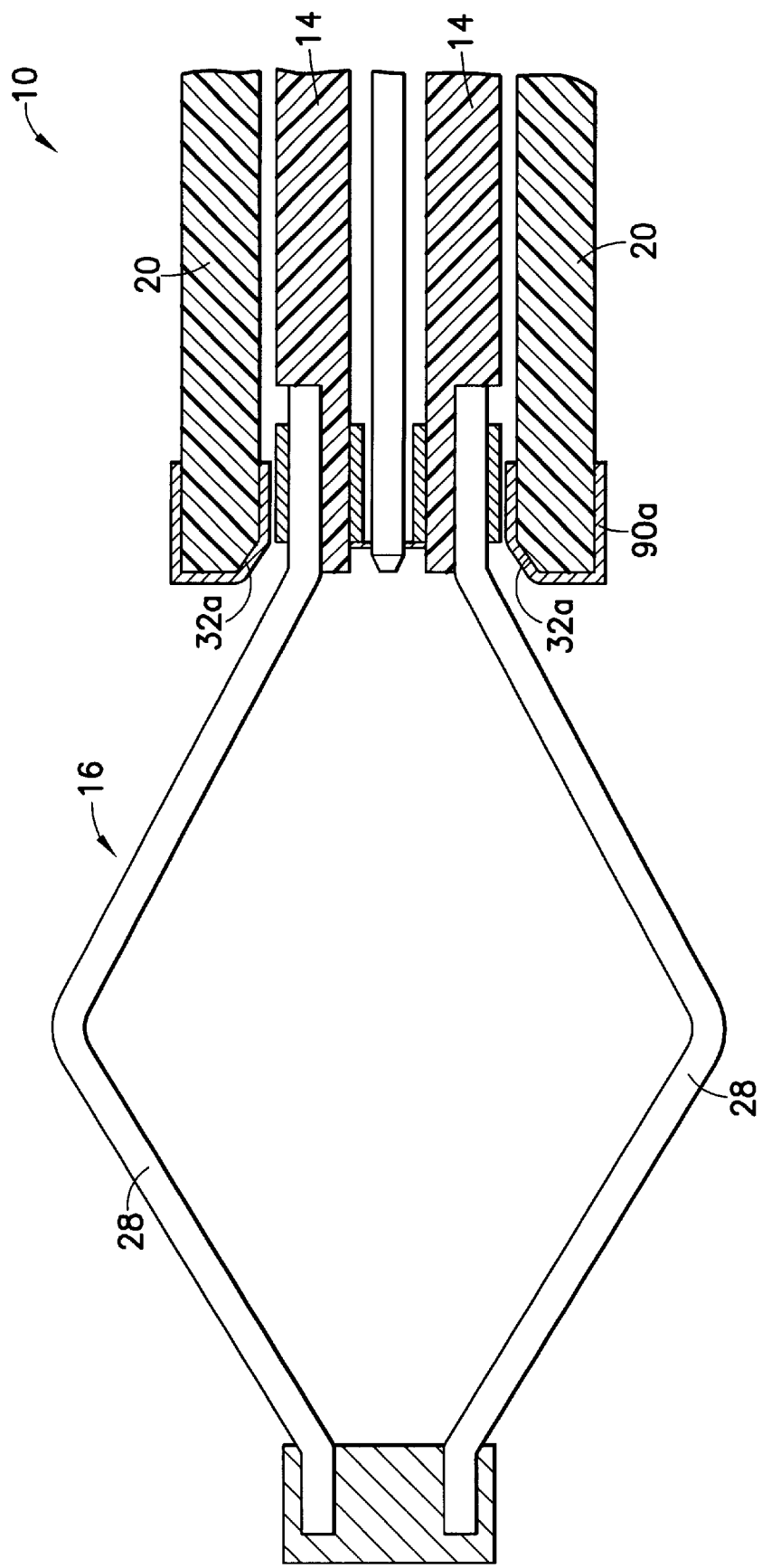
FIG. 6 is a broken cross-sectional view of the first embodiment of the invention showing a second preferred aspect of the invention.

When the shaft 14 and basket assembly 16 are moved distally, the pre-formed and expanded members 28 of the basket assembly 16 place considerable force upon the distal end 32 of the sheath 20 and can potentially cause the distal end 32 of the sheath 20 to split. Therefore, according to a first preferred aspect of the invention and as shown in FIGS. 5 and 6, the distal end 32 of the sheath 20 may be provided with a distal reinforcing sleeve or reinforcing cover 90 to strengthen the distal end 32 of the sheath 20 and prevent it from splitting. The wall thickness of the sleeve 90 is preferably between 0.005 inch and 0.015 inch. The material forming the sleeve 90 can be stainless steel, or a denser material such as gold or platinum-iridium to increase the radiopacity of the distal end 32 of the sheath 20. Alternately or additionally, according to a second preferred aspect of the invention as shown specifically in FIG. 6, the distal end 32a of the sheath 20 may be ramped to reduce stress on the distal end 32a of the sheath 20 and better guide the basket assembly 16 into and out of the sheath 20. A similarly shaped sleeve 90a is utilized.

Figure 7:
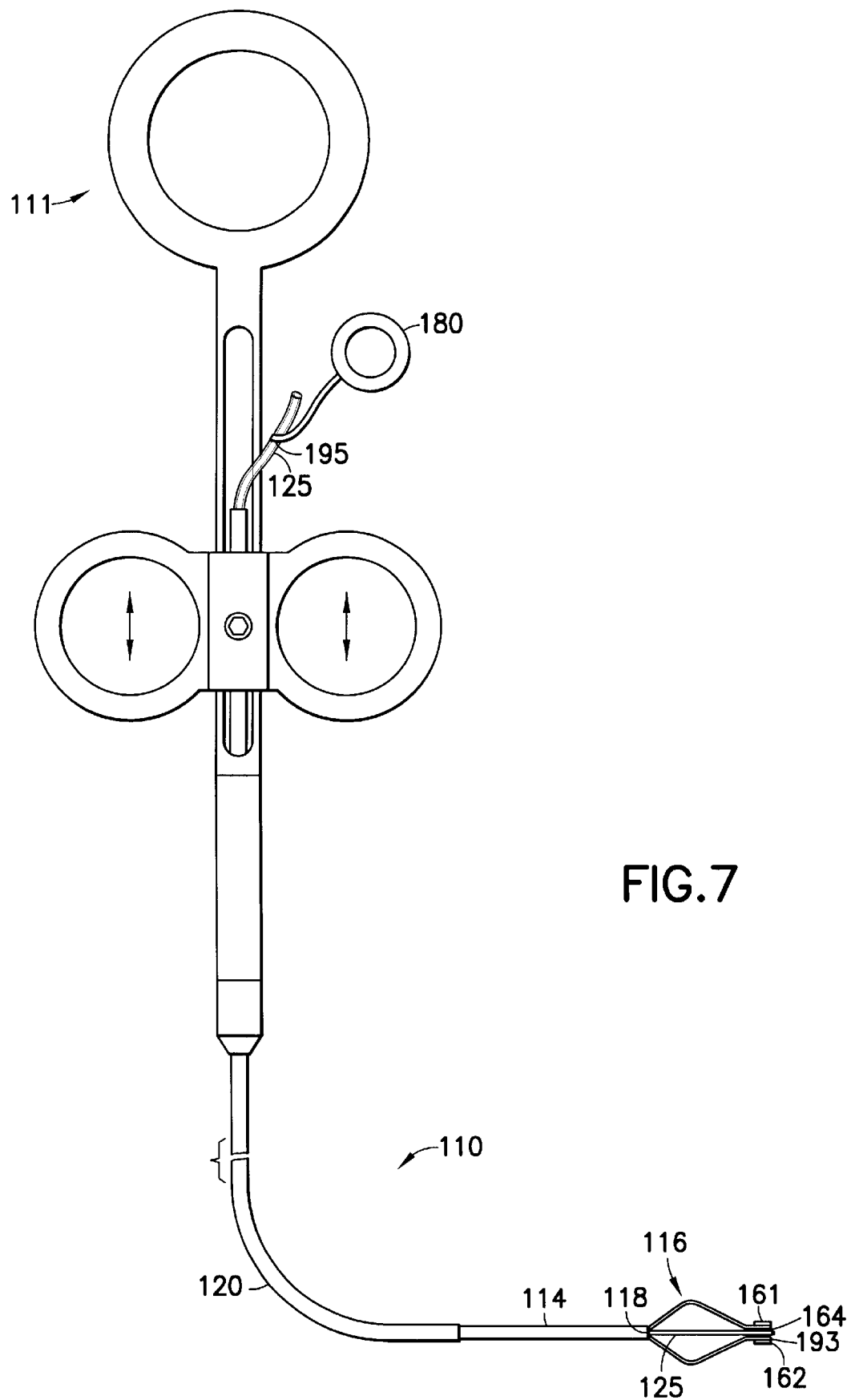
FIG. 7 is a partial broken side elevation of an exemplary second embodiment of the surgical basket instrument according to the invention.
Figure 8:
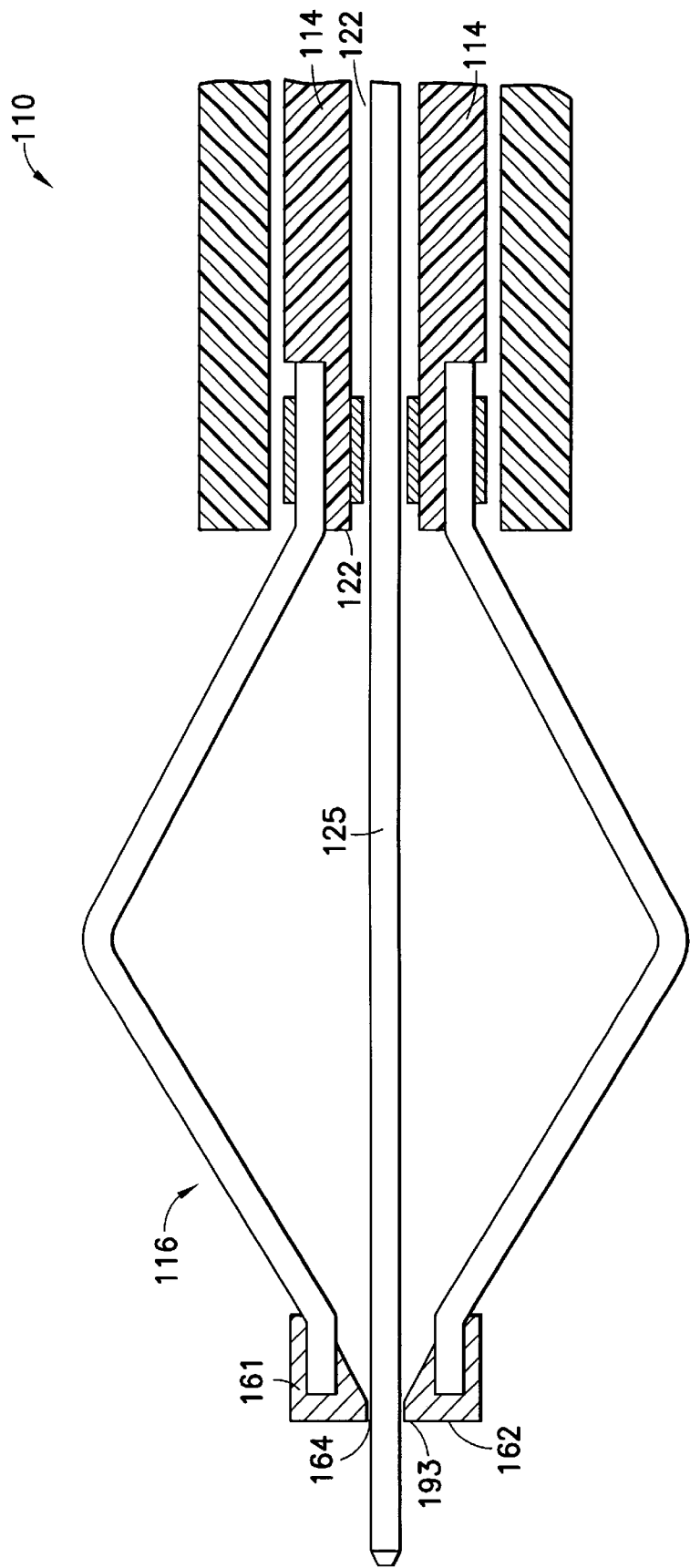
FIG. 8 is a broken cross-sectional view of the distal end of a second embodiment of the surgical basket instrument according to the invention, with a fiber optic extended beyond a distal end of the instrument.

Referring now to FIGS. 7 and 8, a second embodiment of the surgical basket instrument 110 which is substantially similar to the first embodiment 10 (with like parts having reference numerals incremented by 100), is shown. According to the second embodiment of the invention, the fiber optic 125 is not fixed to the shaft 114 and is instead axially movable relative to the shaft 114. A fourth finger ring 180 coupled to the proximal end 195 of the fiber optic 125 at the proximal handle 11 is used to position and maneuver the fiber optic 125 axially relative to the shaft 114. In the second embodiment, no shield is provided blocking the channel 122 at the distal end 118 of the shaft 114. Further, a central opening 164 is defined in the distal ferrule 161 providing access beyond a distal end 193 of the instrument 110. According to the second embodiment 110, the fiber optic 125 may be extended into the basket assembly 116 and optionally through the central opening 164, thereby providing capability beyond the distal end 193 of the instrument 110. The second embodiment of the basket instrument 110 can therefore also be used as a sphinctertome, for cutting into a bile duct sphincter or other similar structure to provide access for the basket assembly 116.

Figure 9:
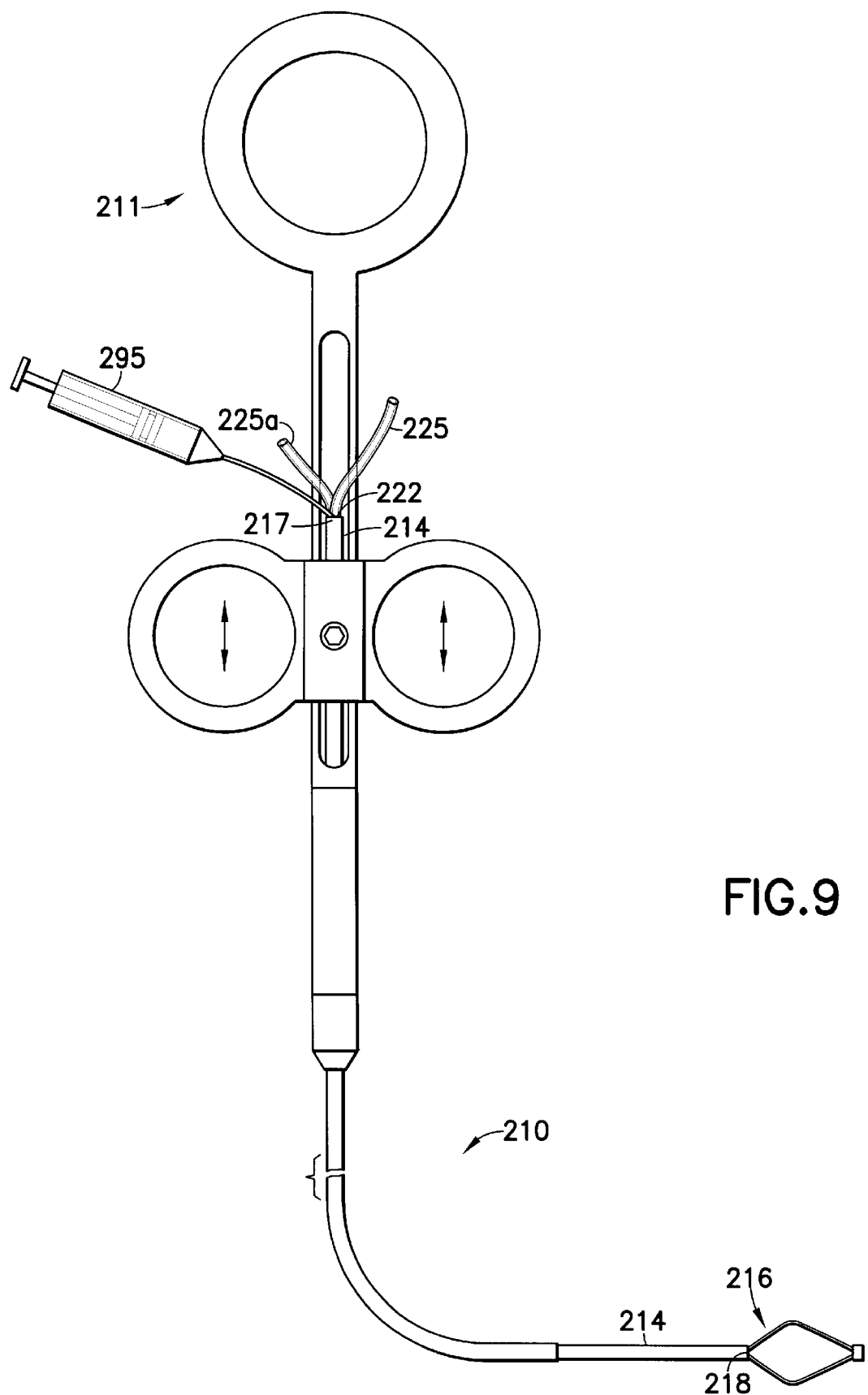
FIG. 9 is a partial broken side elevation of an exemplary third embodiment of the surgical basket instrument according to the invention.
Figure 10:
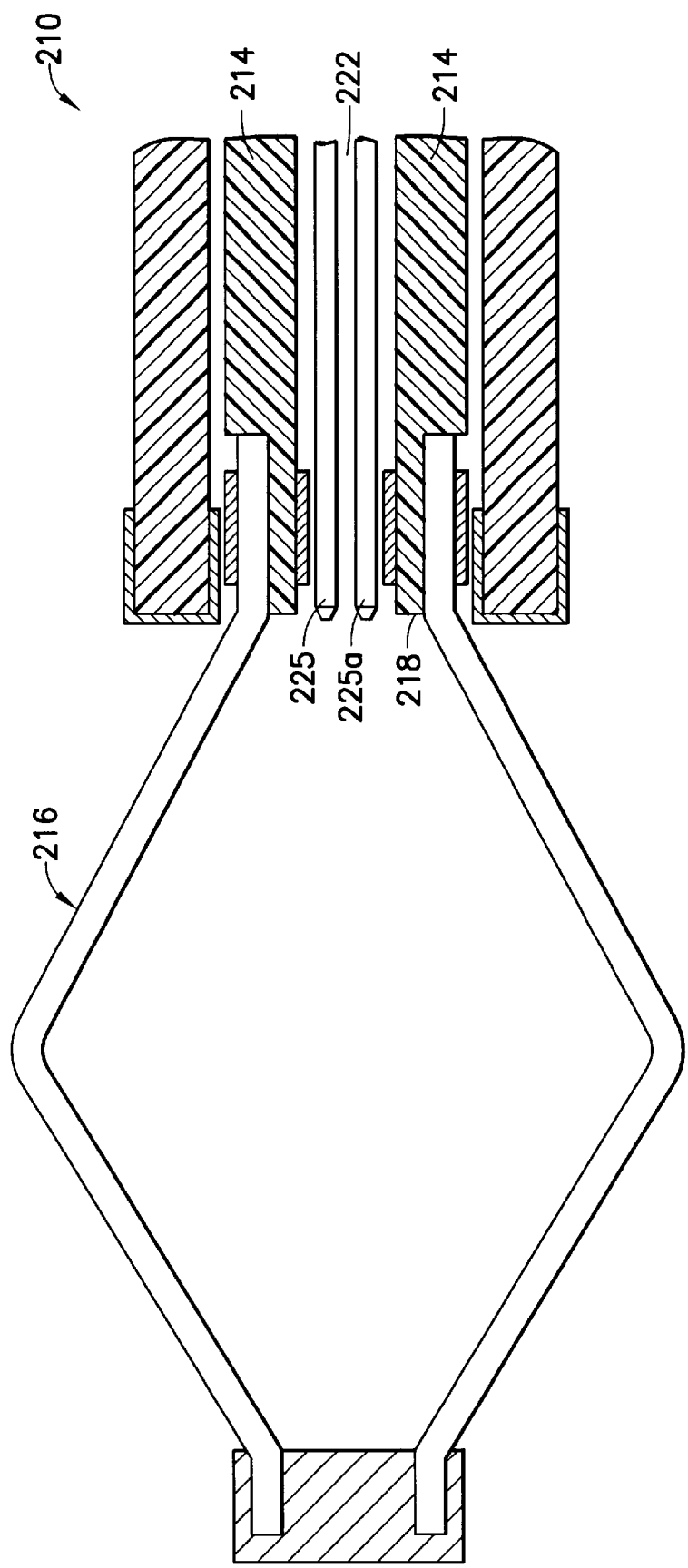
FIG. 10 is a broken cross-sectional view of the distal end of the third embodiment of the surgical basket instrument according to the invention, having multiple fiber optics and with a basket assembly extended.

Referring now to FIGS. 9 and 10, a third embodiment of the surgical basket instrument 110 which is substantially similar to the first embodiment 110 (with like parts having reference numerals incremented by 200), is shown. According to the third embodiment of the invention, at least two optical fibers 225, 225a are provided. One or more of the fiber optics may be fixed relative to the channel 222 (as in the first embodiment of the invention) so that they extend only to the distal end 218 of the shaft 214. Alternately, as in the second embodiment of the invention, one or more of the fiber optics 225, 225a could be permitted to move relative to the shaft. One of the fiber optics is preferably coupled to a light source and is used for illuminating the distal end of the instrument. The other fiber optic is preferably coupled to a viewing mechanism. In addition, a third fiber optic (not shown), or either of the fibers 225, 225a may be adapted for coupling to a laser (not shown) so that in addition to providing the instrument with an endoscopic type viewing capability, the instrument can be used for providing laser energy to break the calculi contained within the basket assembly 216. Referring specifically to FIG. 9, in order to prevent build-up of bile, blood, or other material which would prevent proper viewing at the distal end of the instrument, a proximal syringe 295 (or other pump) containing fluid is provided adjacent the proximal handle 211. The syringe 295 is in fluid communication with the channel 222 of the shaft 214, and is adapted to inject the fluid into the channel 222 at the proximal end 217 of the shaft 214, thereby flushing the channel 222 and the distal end of the instrument.

Figure 11:
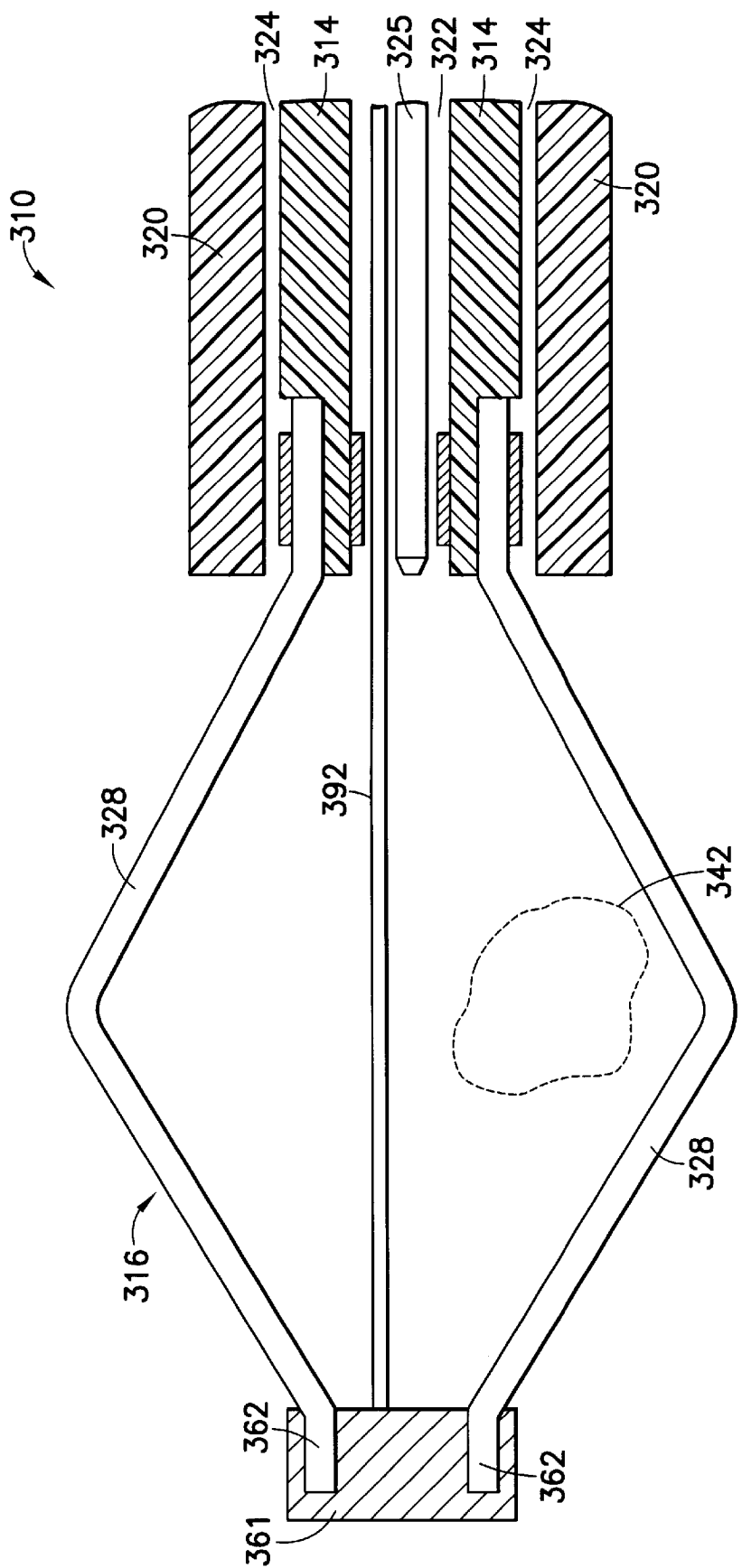
FIG. 11 is a broken cross-sectional view of the distal end of a fourth embodiment of the surgical basket instrument of the invention.

Referring now to FIG. 11, a fourth embodiment of the surgical basket instrument 310 which is substantially similar to the first embodiment 10 (with like parts having reference numerals incremented by 300), is shown. According to the fourth embodiment of the invention, an actuating wire 392 extends through the channel 322 of the shaft 314 from the proximal end of the shaft 314 and is coupled to the crimp band, cap, or distal ferrule 361 coupling the distal ends 362 of the members 328. The actuating wire 392 runs substantially through the channel 322 of the shaft 314 to the distal end 362 of the basket 316 and operates to move the distal ends 362 of the members 328 axially relative to the shaft 314 thereby providing a force to open and close the members 328 of the basket assembly 316. This facilitates capture of larger or smaller calculi 342, aids in securing smaller calculi within the basket 316, and aids in crushing larger calculi into more manageably sized particles. The actuating wire 392 is actuated by an additional movable finger piece (not shown) at the handle. The actuating wire 392 is preferably formed from stainless steel or Nitinol, and may be formed as a twisted and drawn cable (as previously described with reference to the shaft). Additionally, according to the fourth embodiment 310, a fiber optic 325 extending through the channel 322 is preferably provided; however, no fiber optic 325 need be provided.

Figure 12:
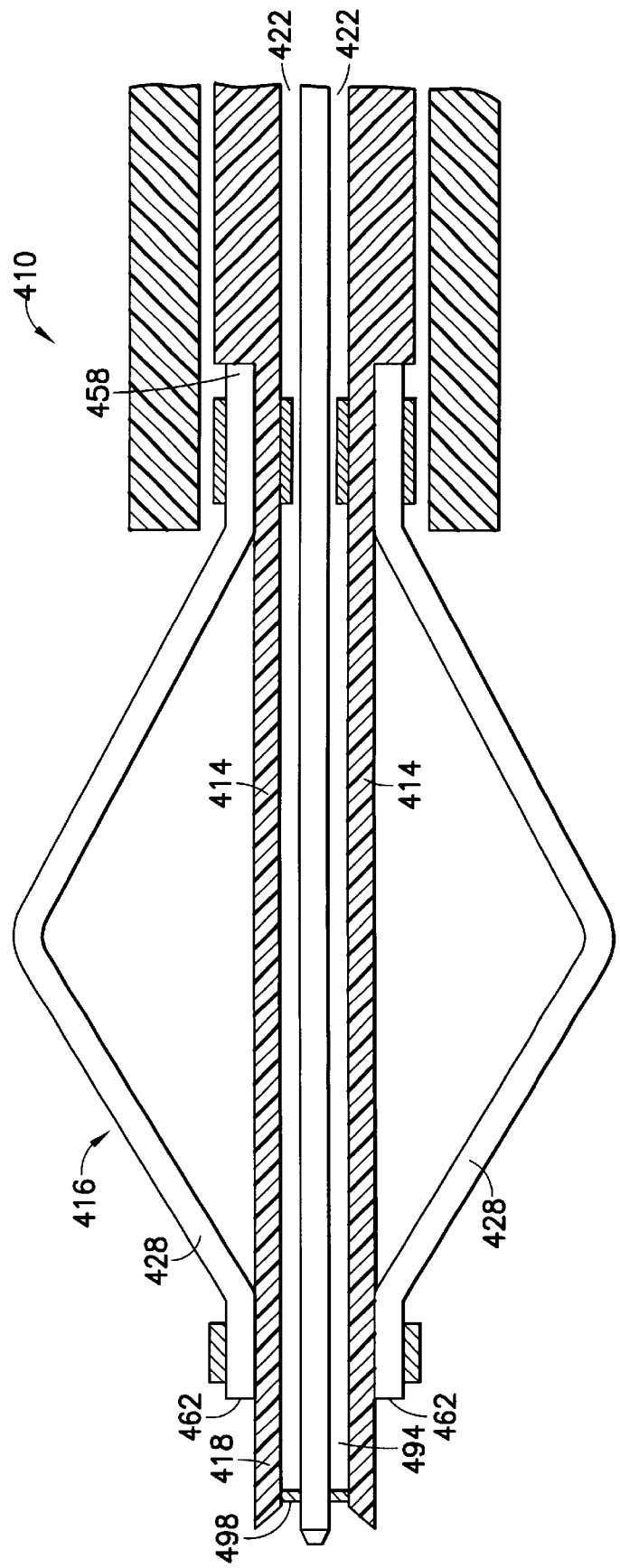
FIG. 12 is a broken cross-sectional view of the distal end of a fifth embodiment of the surgical basket instrument of the invention.

Referring now to FIG. 12, a fifth embodiment of the surgical basket instrument 410 which is substantially similar to the first embodiment 10 (with like parts having reference numerals incremented by 400), is shown. In the fifth embodiment, rather than ending at the proximal end 458 of the basket assembly 416, the shaft 414 extends through the basket assembly 416 and through a distal opening 494 defined between the members 428 at the distal end 462 of the members 428. The proximal end 458 of the basket assembly 416 is coupled to the shaft 414 as described in the first embodiment 10. The dista:l ends 462 of the pre-formed members 428 forming the basket assembly 416 are coupled to each other about the shaft 414 but not secured to the shaft 414 such that they can move (or ride) in unison axially along the shaft 414. As with the first embodiment 10, a shield 498 may be provided at the distal end 418 of the shaft 414 to prevent bile or fluid from clogging the channel 422.

Figure 13:
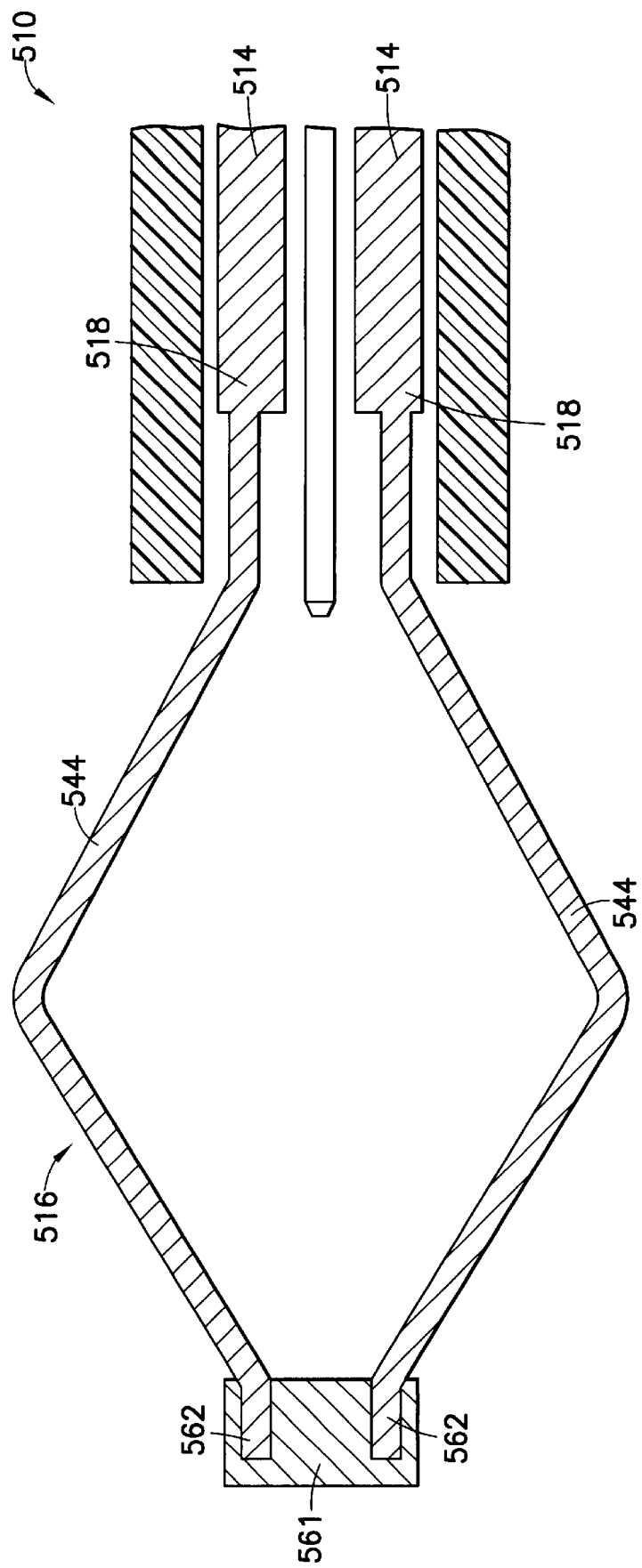
FIG. 13 is a broken cross-sectional view of the distal end of a sixth embodiment of the surgical basket instrument of the invention.

Referring now to FIG. 13, a sixth embodiment of the surgical basket instrument 510 which is substantially similar to the first embodiment 10 (with like parts having reference numerals incremented by 500), is shown. According to the sixth embodiment, the basket assembly 516 is formed by partially untwisting the compacted wires 544 from the distal end 518 of the shaft 514, pre-forming each of the wires 544 (i.e. members) to take a desired expanded shape of the basket assembly 516, and coupling the distal ends 562 together with a crimp band, cap, or ferrule 561 as disclosed in the first embodiment 10 such that the wires 544 will act in unison. This embodiment 510 eliminates the necessity for providing a connector joining the proximal end of the basket assembly 516 to the distal end of the shaft 514.

There have been described and illustrated herein several embodiments of a surgical basket instrument, basket assemblies for the instrument, and actuation handles for operation of the instrument. While particular embodiments of the invention have been described, it is not intended that the invention be limited thereto, as it is intended that the invention be as broad in scope as the art will allow and that the specification be read likewise. Thus, while particular embodiments were shown, it will be appreciated that different aspects of the different embodiments may be used together. Also, while particular aspects of the invention were shown, modifications may be made. Thus, while it is preferable to form the shaft from a hollow nickel-titanium cable, it will be understood that other of a variety of shape memory materials may instead be used to form the hollow cable including but not limited to: stainless steel and alloys thereof, Ni—Ti, Ag—Zn, Au—Cd, Au—Cu—Zn, Cu—Al, Cu—Al—Ni, Cu—Au—Zn, Cu—Sn, Cu—Zn, Cu—Zn—Al, Cu—Zn—Ga, Cu—Zn—Is, Cu—Zn—Sn, Fe—Pt, In—Ti, Ni—Al, Ni—Al, Ni—Ti—X (where X is a ternary element), Ti—Co—Ni, Ti—Cu—Ni. For each of the foregoing basket embodiments, the basket may instead be comprised of differently manufactured members. For example and not by way of limitation, the basket may be comprised of both twisted cables and cables made form multiple wires which are twisted and drawn, solid wires and twisted cables, a combination of solid wires and twisted and drawn cables, monofilament synthetic strands (e.g., nylon line) and solid wires, and a combination of low Z twisted and drawn cables and high Z twisted and drawn cables. It will be appreciated that yet other material and structural combinations may also be used; i.e., any combination of twisted cables, twisted and drawn cables (using relatively high and/or low Z materials), wires, and monofilaments. In addition, a basket comprised of one or more members of a first diameter may be used with one or more members of a second diameter different than the first diameter. Basket assemblies with differently constructed members enable a basket of great versatility; i.e., enhanced cannulation capability with better dilation of the duct and improved crushing force to crush calculi. Further, crushing force may also be enhanced by utilizing a basket assembly formed from members having a non-circular cross-sectional shape. One preferred cross-sectional shape is a teardrop shape having an edge, with the edge of each strand being directed radially inward to reduce the surface area of the members available for contact against a calculi provided within the basket assembly. While a proximal actuation handle has been disclosed, it will be appreciated that no actuation handle is required and the shaft, the fiber optic, and the sheath may be manually moved axially relative to each other. Alternately, a different handle system (e.g. where the sheath is moved and the shaft is fixed) may be utilized. In addition, while the basket instrument has been described with respect to removing calculi from the gastrointestinal and urological ducts, it will be appreciated that the instrument may be used within the vascular system to remove materials provided therein. It will therefore be appreciated by those skilled in the art that yet other modifications could be made to the provided invention without deviating from its spirit and scope.

What is claimed is:

1. A surgical basket instrument, comprising:
   a) a shaft having a proximal end and a distal end, said shaft formed from a cable, having a channel defined axially therethrough;
   b) a sheath having a proximal end and a distal end and substantially surrounding said shaft, said sheath having a sheath diameter, said shaft movable axially relative to said sheath;
   c) a basket assembly having a proximal end and a distal end and including a plurality of members coupled substantially circumferentially about said shaft, said members defining spaces therebetween, said basket assembly being expandable to a diameter greater than said diameter of said sheath, said basket assembly being collapsible to fit within said sheath, said basket assembly being axially slidable within said sheath; and
   d) at least a first fiber optic having a proximal end and a distal end and adapted to receive one of a proximally coupled laser and a proximally coupled optical scope, said at least a first fiber optic being generally within said channel of said shaft.

2. A surgical basket instrument according to claim 1, further comprising:
   e) a handle having a stationary piece and a movable piece, said proximal end of said sheath coupled to said stationary piece, said proximal end of said shaft coupled to said movable piece, said movable piece movable axially relative to said stationary piece, said handle adapted to move said shaft axially relative to said sheath.

3. A surgical basket instrument according to claim 1, wherein:
   said proximal end of said basket assembly is coupled adjacent said distal end of said shaft by one of a crimp band and a ferrule, and said members are coupled adjacent said distal end of said basket assembly.

4. A surgical basket instrument according to claim 3, wherein:
   said distal end of said basket assembly defines a central opening into said basket assembly, and said shaft and said at least a first fiber optic extend through said central opening in said distal end of said basket assembly.

5. A surgical basket instrument according to claim 1, wherein:
   said members of said basket assembly are pre-formed from a flexible shape memory material, said basket assembly is self-expandable when released from within the sheath, and collapsible when retracted within said sheath.

6. A surgical basket instrument according to claim 5, wherein:
   said shape memory material is one of nickel-titanium and a nickel-titanium alloy.

7. A surgical basket instrument according to claim 1, wherein:
   said shaft is made from a plurality of metal strands twisted about a wire and then compacted.

8. A surgical basket instrument according to claim 7, wherein:
   said metal strands are shape memory metal strands.

9. A surgical basket instrument according to claim 8, wherein:
   said shape memory metal is nickel-titanium.

10. A surgical basket instrument according to claim 1, wherein:
    a protective sleeve is coupled to said distal end of said sheath.

11. A surgical basket instrument according to claim 1, wherein:
    a shield is provided across a distal end of said shaft surrounding but not blocking said fiber optic and substantially blocking said channel of said shaft.

12. A surgical basket instrument according to claim 2, wherein:
    said shaft and said basket assembly are both axially and rotatably movable within said sheath, and said handle is adapted to rotatably move said shaft and said basket relative to said sheath.

13. A surgical basket instrument, comprising:
    a) a shaft having a proximal end and a distal end, said shaft formed from a cable having a channel defined axially therethrough;
    b) a sheath having a proximal end and a distal end and substantially surrounding said shaft, said sheath having a sheath diameter, said shaft movable axially relative to said sheath;
    c) a basket assembly having a proximal end and a distal end and including a plurality of members coupled substantially circumferentially about said shaft, said members defining spaces therebetween, said members of said basket assembly are pre-formed from a flexible shape memory material, said basket assembly being self-expandable when released from within the sheath, said basket assembly being expandable to a size greater than said diameter of said sheath, said basket assembly being collapsible to fit within said sheath, said basket assembly axially and rotatably movable within said sheath; and d) a handle having a stationary piece and a movable piece, said proximal end of said sheath coupled to said stationary piece, said proximal end of said shaft coupled to said movable piece, said movable piece movable axially relative to said stationary piece, said handle adapted to move said shaft axially relative to said sheath.

14. A surgical basket instrument according to claim 13, further comprising:

e) a plurality of fiber optics each having a proximal end and a distal end, each of said plurality of fiber optics being generally within said channel of said shaft.

15. A surgical basket instrument according to claim 14, further comprising:

f) a fluid source coupled to and in fluid communication with said channel of said shaft.

16. A surgical basket instrument according to claim 14, wherein:

at least one of said plurality of fiber optics is axially movable relative to said shaft, said distal end of said at least one of said plurality of fiber optics is extendable beyond said distal end of said shaft and extendably beyond said distal end of said basket assembly of the instrument.

17. A surgical basket instrument according to claim 14, wherein:

a first of said plurality of fiber optics is adapted to couple to a light source, a second of said plurality of fiber optics is adapted to couple to a scope, and at least one of said fiber optics is adapted to be coupled to a laser.

18. A surgical basket instrument according to claim 13, wherein:

said proximal end of said basket assembly is coupled adjacent said distal end of said shaft by one of a first crimp band and a first ferrule, and said members are coupled adjacent said distal end of said basket assembly by a distal cap.

19. A surgical basket instrument according to claim 18, further comprising:

e) an actuating wire coupled proximally adjacent said handle and distally to said distal cap adjacent said distal end of said basket assembly, said actuating wire being generally within said channel.

20. A surgical basket instrument according to claim 13, wherein:

said shaft is made from a plurality of metal strands twisted about a wire and then compacted.

21. A surgical basket instrument according to claim 20, wherein:

said metal strands are a shape memory material.

22. A surgical basket instrument according to claim 21, wherein:

said shape memory material is nickel-titanium.

23. A surgical basket instrument according to claim 13, wherein:

said shaft and said basket assembly are both axially and rotatably movable within said sheath and said handle is adapted to rotatably move said shaft and said basket relative to said sheath.

24. A surgical basket instrument, comprising:

a) a shaft having a proximal end and a distal end, said shaft formed from a cable having a channel defined axially therethrough, said cable formed from a plurality of metal strands twisted about a wire and then compacted, said channel formed by removing said wire;

b) a sheath having a proximal end and a distal end and substantially surrounding said shaft, said sheath having a sheath diameter, said shaft movable axially relative to said sheath; and c) a basket assembly having a proximal end extending from said shaft and a distal end, said basket assembly formed from said plurality of metal strands of said shaft such that said strands are substantially circumferentially positioned with spaces defined therebetween, said basket assembly being axially slidable within said sheath.

25. A surgical basket instrument according to claim 24, further comprising:

d) a handle having a stationary piece and a movable piece, said proximal end of said sheath coupled to said stationary piece, said proximal end of said shaft coupled to said movable piece, said movable piece movable axially relative to said stationary piece, said handle adapted to move said shaft axially and rotatably relative to said sheath.

26. A surgical basket instrument according to claim 24, further comprising:

d) a fiber optic having a proximal end and a distal end and adapted to receive a proximally coupled laser, said fiber optic being generally within said channel of said shaft.

27. A surgical basket instrument according to claim 24, wherein:

said proximal end of said basket assembly is coupled adjacent said distal end of said shaft by one of a first crimp band and a first ferrule, and said members are coupled adjacent said distal end of said basket assembly by a distal cap.

* * * * *